United States Patent [19]

Öste et al.

[11] Patent Number: 5,898,792
[45] Date of Patent: Apr. 27, 1999

[54] METHODS AND DEVICES FOR AUTOMATIC ASSESSMENT OF CORN

[75] Inventors: Rickard Öste; Peter Egelberg; Carsten Peterson, all of Lund; Eivor Svensson, Hjärup; Olle Mønsson, Malmö, all of Sweden

[73] Assignee: Agrovision AB, Lund, Sweden

[21] Appl. No.: 08/714,095

[22] PCT Filed: Mar. 17, 1995

[86] PCT No.: PCT/SE95/00268

§ 371 Date: Nov. 5, 1996

§ 102(e) Date: Nov. 5, 1996

[87] PCT Pub. No.: WO95/25273

PCT Pub. Date: Sep. 21, 1995

[30] Foreign Application Priority Data

Mar. 17, 1994 [SE] Sweden .................................. 9400919

[51] Int. Cl.⁶ ..................................................... G06K 9/00
[52] U.S. Cl. .......................................... 382/110; 382/165
[58] Field of Search ..................................... 382/100, 110, 382/156, 165; 348/89; 73/169; 209/576, 580, 581, 582; 706/904, 912

[56] References Cited

U.S. PATENT DOCUMENTS

| | | | |
|---|---|---|---|
| 4,260,262 | 4/1981 | Webster | 356/418 |
| 4,713,781 | 12/1987 | Brizgis et al. | 364/552 |
| 4,975,863 | 12/1990 | Sistler et al. | 364/555 |
| 5,321,764 | 6/1994 | Cullen et al. | 382/1 |

FOREIGN PATENT DOCUMENTS

| | | | |
|---|---|---|---|
| 2416465 | 10/1979 | France | B02B 3/14 |
| 470 465 | 4/1994 | Sweden | G06F 15/70 |

OTHER PUBLICATIONS

Zayas et al., "Discrimination Between Wheat Classes and Varieties by Image Analysis," *Cereal Chemistry*, vol. 63, No. 1, 1986, pp. 52–56.

Chen et al., "Relation of Kernal Color to Wheat Class and Grade," *Cereal Science Today*, vol. 17, No. 11, Nov. 1972, pp. 340–343.

Neuman et al., "Discrimination of Wheat Class and Variety by Digital Image Analysis of Whole Grain Samples," *Journal of Cereal Science*, vol. 6, 1987, pp. 125–132.

Winter et al., "Discrimination of Hard-to-Pop Popcorn Kernels by Machine Vision and Neural Network," Paper No. Mansask 96–107 presented at the 1996 North–Central Intersectional ASAE/CSAE Meeting, Sep. 27–28 1996.

D. R. Marshall et al., *Aust. J. Agric. Res.*, vol. 37, pp. 331–342, 1986, "Effects of Grain Shape and Size on Milling Yields in Wheat II—Experimental Studies".

*Primary Examiner*—Andrew W. Johns
*Attorney, Agent, or Firm*—Birch, Stewart, Kolasch & Birch, LLP

[57] ABSTRACT

The flour yield, protein content and bulk density of cereal kernels can be determined by producing images of the cereal kernels, at least one color parameter and/or at least one geometric parameter are determined for the cereal kernels, and input signals to a neural network are produced by means of the color parameter and/or the geometric parameter. If the neural network is trained in some suitable manner, it can determine the flour yield, protein content and bulk density on the basis of the input signals.

29 Claims, 7 Drawing Sheets

Protein Content (weight-%)

GrainCheck (TKW, 13 Color var.)

METHODS AND DEVICES FOR AUTOMATIC ASSESSMENT OF CORN

METHODS AND DEVICES FOR AUTOMATIC ASSESSMENT OF CORN

The present invention relates to methods and devices for determining the flour yield, the protein content and the bulk density for a plurality of cereal kernels.

The flour yield is defined as the amount of flour obtained from an amount of corn of a given weight, for instance one tonne, and is expressed in % by weight. When purchasing corn for a flour mill, it is desirable to be able to predict the flour yield for different corn consignments, thereby making it possible to select the consignments that give the highest flour yield and, thus, the largest profits for the flour mill.

Today, the flour yield is predicted by determining the bulk density (also called volumetric weight) for a sample from the corn consignment. Generally, one litre of kernels of the corn concerned is simply weighed. It is in fact considered that the bulk density provides a rough measure of the flour yield.

In the article "Effects of Grain Shape and Size on Milling Yields in Wheat" by D. R. Marshall, D. J. Mares, H. J. Moss and F. W. Ellison in Aust. J. Agric. Res., 1986, 37, p. 340, it is, however, said that the correlation between bulk density and flour yield depends on both the site and the kind of corn and that the bulk density thus cannot be used to reliably predict the flour yield.

In the patent literature, there are examples of experiments of determining the flour yield in other ways than by means of the bulk density.

For example, FR 2,416,465 discloses an instrument for transillumination of corn samples and determination of the flour yield by the transmitted light.

The results obtained by means of this instrument are not known. However, it may be established that there is today no commercially available and practically applicable alternative to using the bulk density, if the flour yield is to be determined.

The above-mentioned article by Marshall, Mares, Moss and Ellison describes an investigation of the effects of the size and shape of the cereal kernels on the flour yield. In the discussion on p. 340, it is stated that the effect of the size of the kernels on the flour yield is small compared with the effects of other factors and is not always easy to demonstrate. Of the other parameters investigated (for example protein content, hardness, depth of crease, bran-layer thickness), only bulk density showed a significant relationship with flour yield.

A first object of the present invention thus is to provide a method and a device which permit accurate determination of the flour yield for a plurality of cereal kernels before milling.

There is also a great interest in quick and easy determination of the protein content in a consignment of corn. Different end users, for example flour mills, malt-houses and fodder factories, require different protein contents. It would therefore be advantageous if already at an early stage in the handling of corn it would be possible to select consignments of corn having the desired protein content, or possibly mix different consignments so as to obtain the desired protein content.

Today, the protein content is usually determined by analysis using infrared light. The analysis can be carried out on reflected or transmitted infrared light and on entire kernels or on flour.

The article "Relation of Kernel Color to Wheat Class and Grade", Cereal Science Today, Vol. 17, November 1972, describes an investigation in which a Hunter Color Difference Meter is used to measure the colour of wheat in an experiment of specifying the colour of wheat and distinguishing among different wheat grades by objective colour measurements. Simple, multiple and partial correlation techniques are used to evaluate the correlations between the Hunter colour values and the grading factors. Among other things, the correlations between on the one hand the protein content in five different grades of wheat and, on the other hand, the Hunter colour values were studied. The highest correlation, −0.645, was obtained between soft white wheats and the Hunter colour value B (blue-yellow). For other grades of wheat, a correlation in the range of 0.004–0.476 was obtained for the different Hunter colour values. The correlations obtained are too low to make it possible to use the Hunter colour values to determine the protein content of wheat, which is also said in the article.

A second object of the present invention is to provide a method and a device for determining the protein content in a consignment of corn before milling.

As mentioned above, bulk density is today determined by weighing the corn at issue by means of a standardised liter measure. The liter measure is filled and weighed by hand, which is time-consuming and heavy. Since bulk density is the most common ground for paying of corn, it needs to be determined frequently, and it would therefore constitute a great improvement if it could be determined automatically.

The above-mentioned article from Cereal Science Today further investigated the correlations between bulk density and the Hunter colour values. The correlations were in the range of 0.023–0.648 depending on the grade of wheat and the Hunter colour value. Again, the correlations are too weak to permit the bulk density to be accurately predicted, which besides is also said in the article.

A third object of the present invention therefore is to provide a method and a device for automatic determination of the bulk density for a consignment of corn before milling.

A fourth object of the invention is to provide a device which, by a single measuring process, can determine the bulk density, the protein content and the flour yield for a sample of cereal kernels.

The first object is achieved by a method and a device for determining the flour yield, which have the features defined in claims 1 and 15, respectively. The second object is achieved by a method and a device for determining the protein content, which have the features defined in claims 2 and 16, respectively. The third object is achieved by a method and a device for automatic determination of the bulk density, which have the features defined in claims 3, 4 and 17, 18, respectively.

It has been found that there is a connection between on the one hand the flour yield and, on the other hand, the colour and geometry of the cereal kernels. By determining the colour and geometry of the cereal kernels in different consignments of corn having a known flour yield, and supplying this information to, for instance, a neural network, it is possible to train the neural network to predict, with very great accuracy, the flour yield for consignments of corn having an unknown flour yield.

It has also been found that the protein content is related to the colour of the cereal kernels, in particular the dispersion in the colour. The protein content of a consignment of corn can therefore be predicted in a manner corresponding to that for the flour yield by means of, for example, a neural network, if this is trained in some suitable manner.

Also the bulk density can be obtained correspondingly by determining the colour dispersion or the geometry of the cereal kernels.

The determination of bulk density, protein content and flour yield can be quickly and readily carried out. It is effected automatically and is, besides, non-destroying. The determination can be carried out during loading and unloading a consignment of corn by taking a sample from the flow of corn.

The present invention will now be described by means of an embodiment, reference being made to the accompanying drawings in which.

Figure 1:
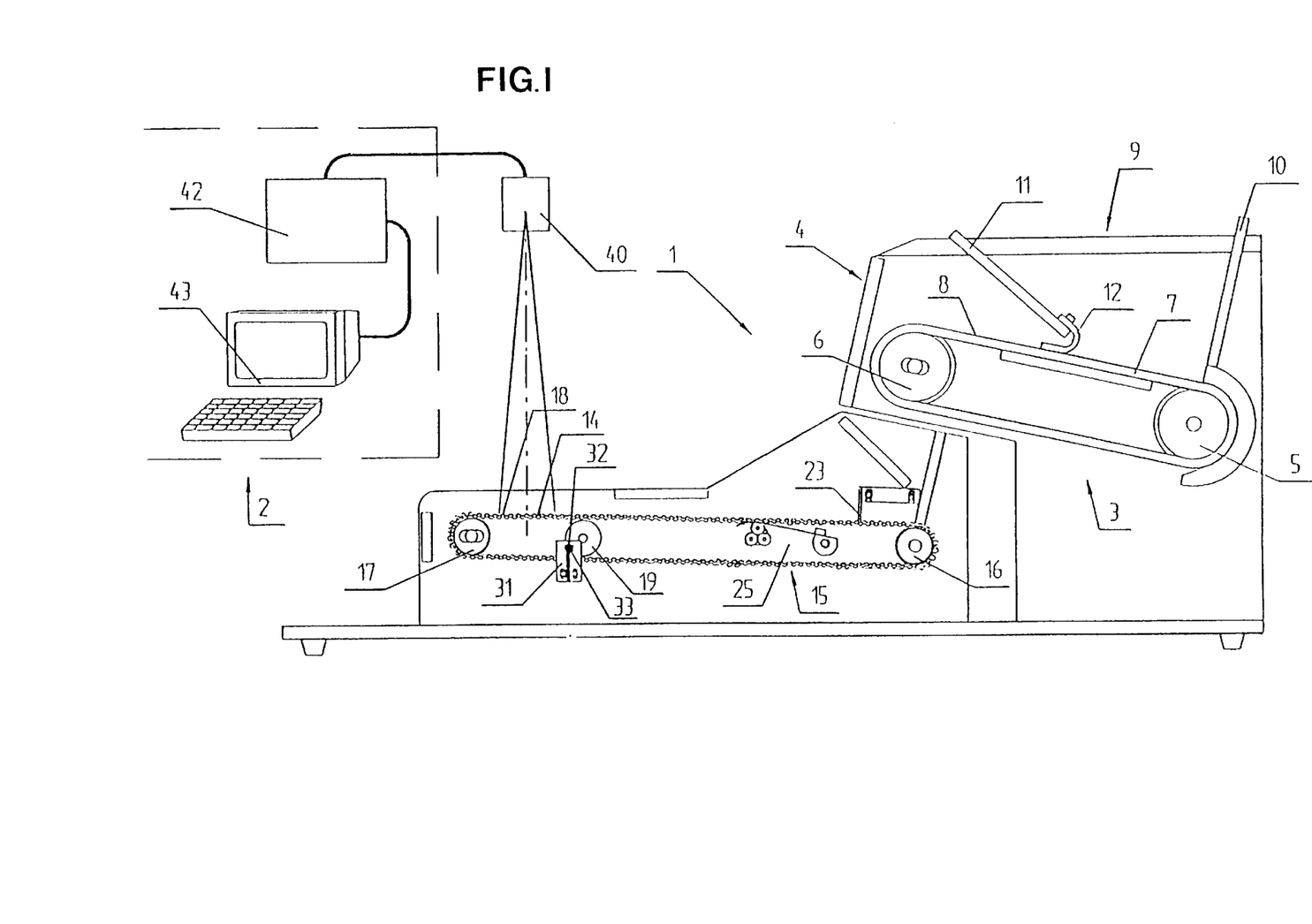
FIG. 1 shows an embodiment of an inventive device, a feeding device being shown in longitudinal section and an image processing device as a block diagram.

In a first embodiment of the invention, a device, as shown in FIG. 1, essentially comprises a feeding device 1, a videocamera 40 and an image processing device 2. The feeding device 1 comprises a first belt conveyor 3 arranged in a casing 4 and having a first wheel 5 driven by a motor (not shown), a second wheel 6 and an endless belt 7 running over the wheels 5, 6. The belt is formed with transverse grooves 8, in which the cereal kernels are portioned out from a store 9 which is contained in the casing and which is filled with samples of cereal kernels. The store 9 comprises two plates 10, 11 which are inclined towards one another, and is besides delimited by the walls of the casing. The lower end of one plate 10 is spaced from the belt 7, and a scraper 12 is attached to this end to take down the cereal kernels into the grooves 8.

A second belt conveyor 15 is arranged vertically and horizontally offset relative to the first belt conveyor 3. The second belt conveyor 15 comprises a first wheel 16 driven by a motor (not shown), a second wheel 17 and an endless belt 18 running over the first and the second wheel 16, 17 in the same direction as the belt 7. The belt 18 is formed with transverse grooves 14 whose width and depth are adjusted to the width and depth of the kernels in a given size interval such that the kernels orient themselves in the longitudinal direction of the grooves. Between the first wheel 16 and the second wheel 17, there is besides a third wheel 19 which engages the belt 18 and whose function will be explained below.

The first wheel 16 of the second belt conveyor 15 is arranged below the second wheel 6 of the first belt conveyor 3 such that cereal kernels can fall down from the first conveyor 3 onto the second conveyor 15 and be spread. A curtain 23 is arranged to pass down the kernels to the grooves 14 of the endless belt 18 and ensure that the kernels form one layer and that they do not essentially overlap each other. Between the first wheel 16 and the third wheel 19 and between the upper and the lower run of the belt 18, there is arranged a vibrator 25, which is arranged to vibrate the upper run of the belt 18 in the vertical direction.

Adjacent to the third wheel 19, which is a gear wheel, there is arranged a pulse generator. This is mounted adjacent the circumference of the third wheel 19 and comprises a light emitter in the form of a light emitting diode 32 and a light receiver in the form of a photocell 33. The pulse generator 31 is connected to a computer 42. When the third wheel 19 rotates in engagement with the belt 18, the pulse generator 31 emits a pulse-shaped signal to the computer 42 in the image processing device 2. This computer 42 controls the motors of the driving wheels 5, 16, the vibrator 25 and the video-camera 40. The third wheel 19 also serves to damp vibrations in the belt 18 in the area between the third wheel 19 and the second wheel 17.

Above the endless belt 18 in its area adjacent the second wheel 17, there is arranged the videocamera 40 in such a manner that images of the belt 18 in the vicinity of the second wheel 17 can be taken. The camera 40 is connected to the image processing device 2, whose design and function will be described in more detail below.

The function of the feeding device 1 will now be described. A sample of cereal kernels is poured onto the first belt conveyor 3 through the store 9. The kernels then form a heap on the belt, but when the belt moves, they will, owing to the upward inclination of the belt and through the scraper 12, be spread portionwise in the grooves 8 of the belt. When the kernels arrive at the second wheel 6, they fall down and are spread on the second belt 18. The kernels positioned on the ridges between the grooves will be passed into the grooves 14 by the curtain 23. Owing to the second belt 18 being vibrated, the advancing kernels will move sideways in the grooves towards the edges of the belt. When the kernels reach the area under the videocamera 40, they will therefore be separated in the longitudinal direction of the belt, be oriented in essentially the same direction and be positioned in essentially one layer on the belt. The kernels will thus overlap each other but to a very small extent. The kernels may, however, lie close together in the grooves 14 in the longitudinal direction thereof.

Each time the computer 42 has counted to a predetermined number of pulses from the pulse generator, a stop signal is emitted, whereby the computer 42 stops all driving motors and the vibrator 25. Then the first and the second belt stop, and the vibrations are discontinued. The computer 42 emits a signal to the videocamera 40 which takes an image of the kernels on the belt 18. Subsequently, the computer starts the motors again, and the feeding of the kernels continues as described above, until a stop signal is again emitted. The predetermined number of pulses after which the stop signal is emitted is selected such that the videocamera will take images of the kernels on the belt which cover the belt without interspaces and without overlappings. In other words, each kernel passing the videocamera will occur in exactly one image, and each image will include a plurality of kernels. It should also be pointed out that the images of the kernels are taken in common visible light.

Alternatively, the belt can be moved continuously and the device can be provided with a stroboscope which together with the camera 40 is controlled such that images are taken of the belt without interspaces and without overlappings.

The image processing device 2 fundamentally comprises the computer 42 connected to the videocamera 40, and a user terminal 43 on whose display device the result of the analysis is presented. In the computer 42, there are, in addition to programs for controlling the motors, the vibrator 25 and the videocamera 40, also programs for determination of flour yield, protein content and bulk density based on the images produced by the videocamera 40. These programs comprise a conversion of the video signals from the camera 40 into suitable input signals to a neural network program which effects the actual determination of flour yield, protein content and bulk density.

When the videocamera 40 has taken an image of the belt, this image is read into the computer and digitised by means of a prior-art so-called frame grabber. The digitised image produced consists of e.g. 512×512 picture elements. The picture elements are represented by RGB representation, i.e. by a value of the intensity of the red colour component, a value of the intensity of the green colour component and a value of the intensity of the blue colour component. Alternatively, some other colour representation may be used.

In the next step, the program locates the kernels in the digitised image. Here use is made of a threshold value of the colour in each picture element. When the value of a picture element exceeds the threshold value, the picture element is assumed to represent a kernel, whereas when the value falls below the threshold value, the picture element is assumed to represent the background, i.e. the belt. In order to obtain a good contrast, the belt 18 can advantageously be blue. The program examines the image point by point, line by line. When it finds a picture element representing a kernel, it examines all neighbouring picture elements. For those picture elements of the neighbouring picture elements which are considered to represent a kernel, the procedure is repeated until all picture elements connected with the first picture element have been identified. Subsequently, the longitudinal axis of the connected picture elements representing a kernel is determined. If the direction of the longitudinal axis deviates by more than a predetermined value from the y axis (vertical axis) of the image, the coherent kernel area is suitably rotated until its longitudinal axis is parallel with the y axis of the image.

When the image of the kernels on the belt is being taken, it may happen that two or more kernels are positioned close together in a groove of the belt or even overlap one another to some extent. The coherent kernel area identified in the image may thus represent more than one kernel. To check whether this is the case, the number of picture elements in x direction (horizontal direction) which represent a kernel is summed up for each y value in the coherent kernel area. The program thus makes a histogram of the number of kernel picture elements in x direction. Then an envelope curve of the histogram is determined, and it is investigated whether there is a minimum between the envelope curve terminal points in y direction. A sufficiently marked minimum indicates that the coherent kernel picture element area actually corresponds to two kernels. If so, the program makes a cut in parallel with the x axis at the minimum of the envelope curve. Subsequently, each part of the coherent kernel picture element area is stored as an image of a kernel. If there are a plurality of minimums, a cut is made at each minimum. After separation, each kernel can, if required, be rotated such that its longitudinal axis conforms with the y axis of the image.

After that, different geometric parameters, such as surface area, length and width, can be determined for each kernel. Moreover, colour parameters, such as mean value and standard deviations for the R, G and B values for the picture elements belonging to each kernel, can be determined. The number of kernels included in an analysed sample can also be determined.

Moreover, the thousand kernel weight is advantageously determined, i.e. the weight of a thousand kernels. To this end, a scale is arranged in connection with the device. The kernels are counted and fed in some suitable manner, for example by blowing with compressed air in the grooves of the belt, to the scale and are weighed. Of course, instead the weight of another predetermined number of kernels can be used. Based on the above-mentioned parameter values, additional parameters can be determined for each kernel, such as intensity and colour saturation which are determined on the basis of the R, G and B values.

The parameter values are gradually stored in a memory. When the parameter values for all kernels have been determined, preferably the mean value and the standard deviation over the entire analysed sample are calculated for each of the determined parameters. Different combinations of these mean values and standard deviations can then suitably be used as input signals to a neural network. The use of mean values and standard deviations as input signals gives the neural network a "survey" of the entire sample, which can be important in, for instance, the determination of the bulk density, in which different size distributions for the kernels can lead to different compacting of the kernels and, thus, different bulk densities. It is also probable that the flour yield is affected by the size distribution for the kernels and, possibly, also by other parameter distributions, and therefore better results can be obtained with input signals to the neural network which mirror the properties of the entire sample.

A neural network is a program consisting of a number of input nodes, in this case one for each input parameter, and a number of output nodes which in this case represent flour yield, protein content and bulk density. Between the input nodes and the output nodes, there are hidden nodes. By supplying input signals representing known corn samples having a known flour yield to the neural network and telling it which flour yield has been obtained for the sample, the neural network can be trained to determine the flour yield. When the neural network has learnt to determine the flour yield, it can be used to determine the flour yield of samples having an unknown flour yield. In the same manner, the neural network can be trained to determine protein content and bulk density. The hidden nodes are sigmoid functions, Gaussian functions or polynomials of high degree, which makes it possible to adapt input data to a substantially arbitrary (linear/non-linear) function. If the classes are linearly dependent on the input nodes, the network is trained to effect a linear adaptation. The neural network method thus comprises linear adaptation as a special case.

By means of the device described above, flour yield, protein content and bulk density for a sample consisting of a plurality of cereal kernels can be quickly and easily determined. A sample of 100 g, i.e. about 2000 kernels, takes about 4 min to analyse.

Below follow examples of predictions of flour yield, protein content and bulk density by means of the present invention for samples having a known flour yield, protein content and bulk density. Each sample contained 100 g of wheat kernels. The samples were run through a device as described above, and an image of each kernel was stored. Each image of the kernel was oriented such that the longitudinal axis of the kernel was parallel with the y axis of the image.

The following parameters were measured for each kernel: The length, which is defined as the largest extent of the kernel in y direction, expressed in the number of picture elements, the width, which is defined as the largest extent of the kernel perpendicular to y direction expressed in the number of picture elements, the surface area of the kernel expressed in the number of picture elements, the R, G and B value for all picture elements included in the image of the kernel, expressed in a unit standardised from 0.0 (black) to 1.0 (full intensity).

By means of the measured values, the following was also determined for each kernel: mean value of and standard deviation for the R, G and B values, and mean value of and standard deviation for colour saturation and intensity of all picture elements included in the image of the kernel.

On the basis of the above-mentioned parameters, the following input signals to the neural network were determined for determination of the flour yield:

1) Standard deviation for the length values of the sample.

2) Standard deviation for the width values of the sample.

3) Standard deviation for the surface area values of the sample.

4) Standard deviation for the R mean values of the sample.

5) Standard deviation for the G mean values of the sample.

6) Standard deviation for the B mean values of the sample.

7) Standard deviation for the colour saturation mean values of the sample.

8) Standard deviation for the intensity mean values of the sample.

9) Mean value for the R standard deviations of the sample.

10) Standard deviation for the R standard deviations of the sample.

11) Mean value for the G standard deviations of the sample.

12) Standard deviation for the G standard deviations of the sample.

13) Mean value for the B standard deviations of the sample.

14) Standard deviation for the B standard deviations of the sample.

15) Mean value for the intensity standard deviations of the sample.

16) Standard deviation for the intensity standard deviations of the sample.

17) Total sum of the lengths of the sample per unit of weight of the sample (g).

18) Total sum of the widths of the sample per unit of weight of the sample (g).

19) Total sum of the surface areas of the sample per unit of weight of the sample (g).

20) Total sum of the R values of the sample per unit of weight of the sample (g).

21) Total sum of the G values of the sample per unit of weight of the sample (g).

22) Total sum of the B values of the sample per unit of weight of the sample (g).

Moreover, the thousand kernel weight (TKW) was determined.

Figure 2:
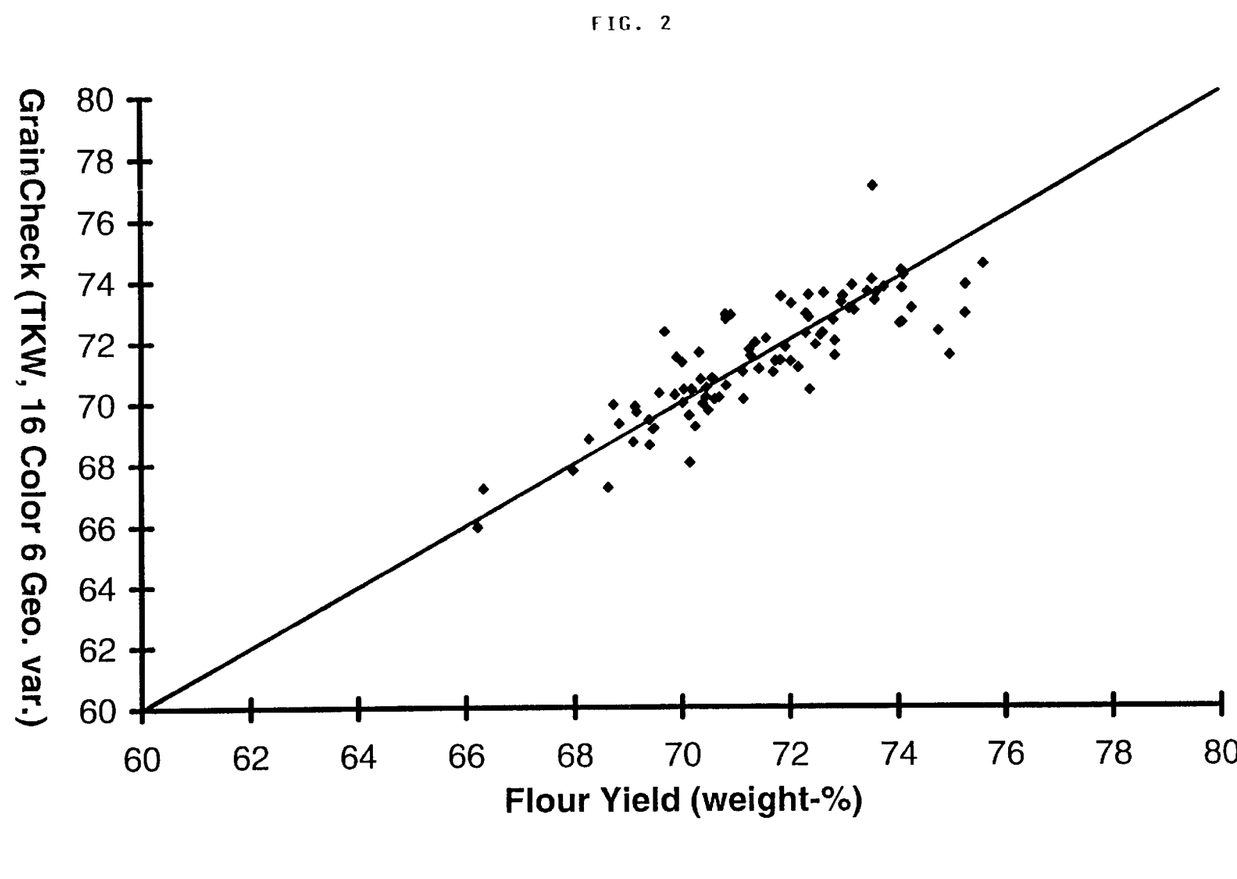
FIG. 2 is a diagram and illustrates the flour yield determined according to the present invention as a function of the actual flour yield.

FIG. 2 shows the result of the determination of the flour yield as a function of the actual flour yield, the actual flour yield being determined by weighing by standard methods of the different flour fractions in connection with the milling operation. The correlation between the flour yield measured according to the known methods and the flour yield determined according to the invention was 0.77.

For determination of the protein content, use was made in a first case of the following colour input signals to the neural network: The input signals Nos 4–16 as above, and the thousand kernel weight.

In a second case, use was made of the following colour input signals: The input signals Nos 8, 15 and 16 of the above-mentioned input signals, and 26) mean value of the intensity mean values of the sample, 27) total sum of the intensity values of the sample per unit of weight (g) of the sample, and the thousand kernel weight.

Figure 3A:
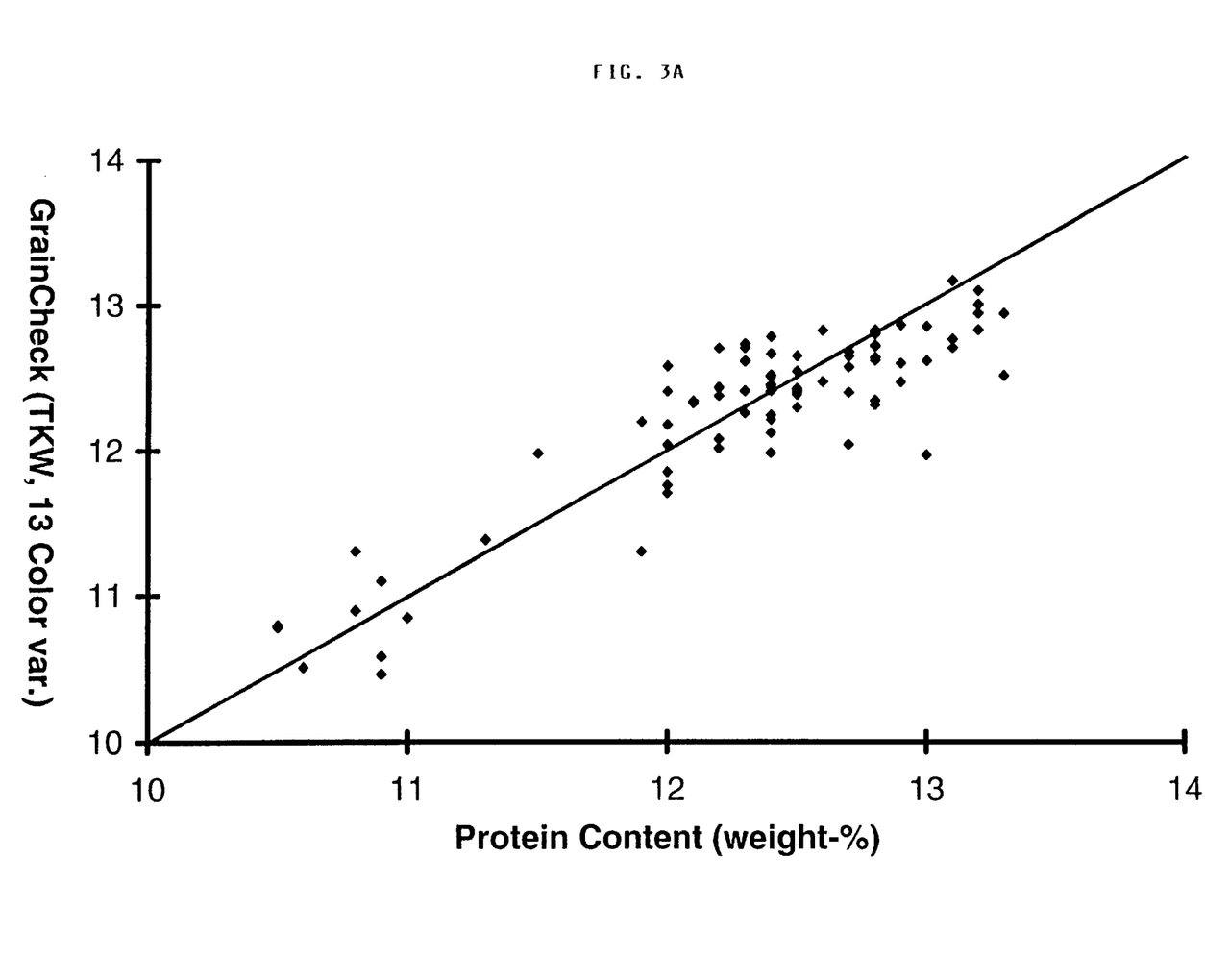
FIGS. 3A and 3B are diagrams and show the protein content determined according to the present invention as a function of the actual protein content by means of a first and a second set of colour input signals.
Figure 3B:
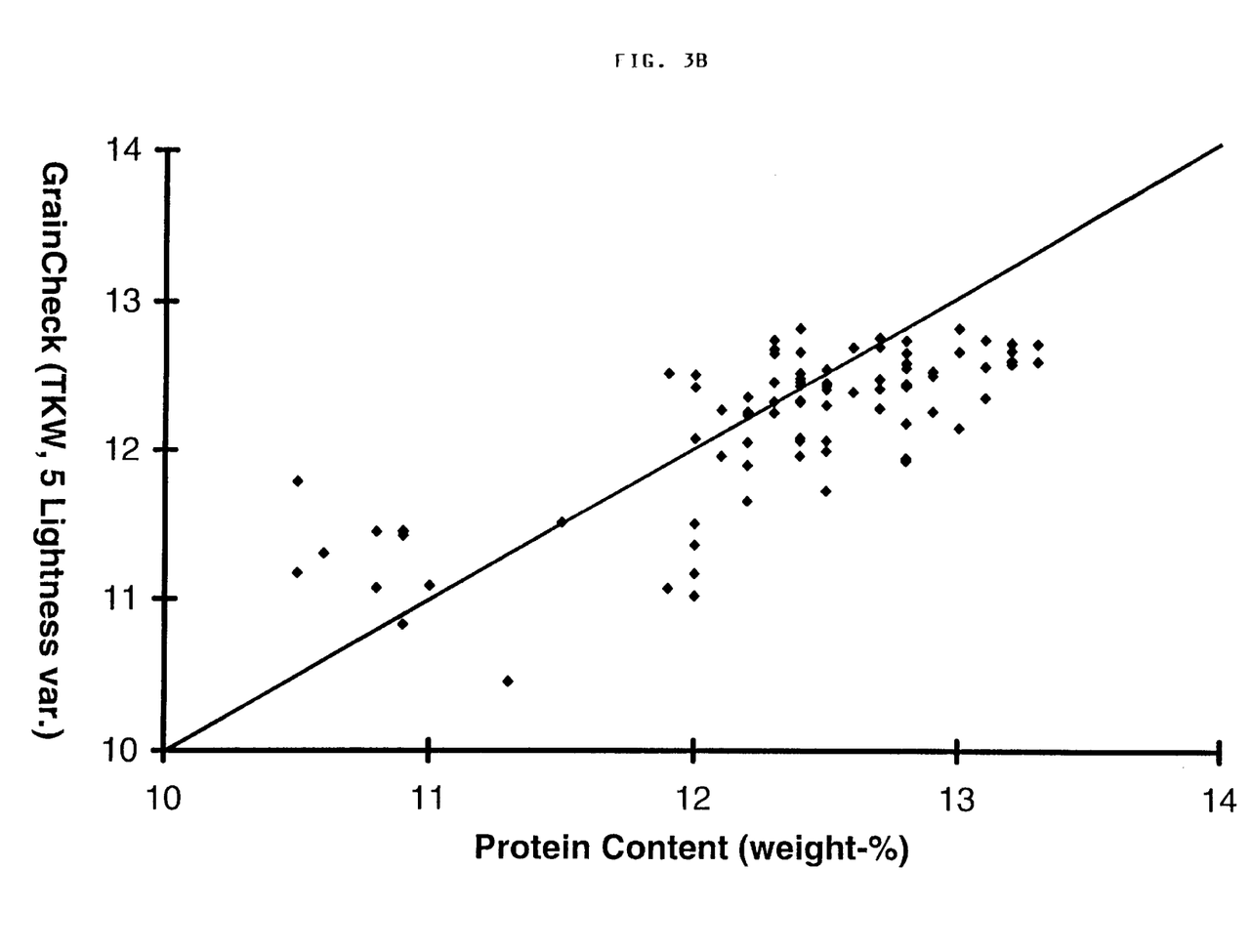

FIGS. 3A and 3B show the result of the determination of the protein content for the different sets of input signals as a function of the actual protein content, the actual protein content being determined by Kjeldahl's method. The correlation was in the first case 0.89 and in the second case 0.75. The correlation increased only slightly, if the following input signals were added in the first case: 20–22 of the above-mentioned input signals, 23) mean value of the R mean values of the sample, 24) mean value of the G mean values of the sample, and 25) mean value of the B mean values of the sample.

For determination of the bulk density, use was made in a first case of the same colour input signals as were used in the first case for the determination of the protein content, i.e. the above-mentioned input signals 4–16 and the thousand kernel weight.

Figure 4A:
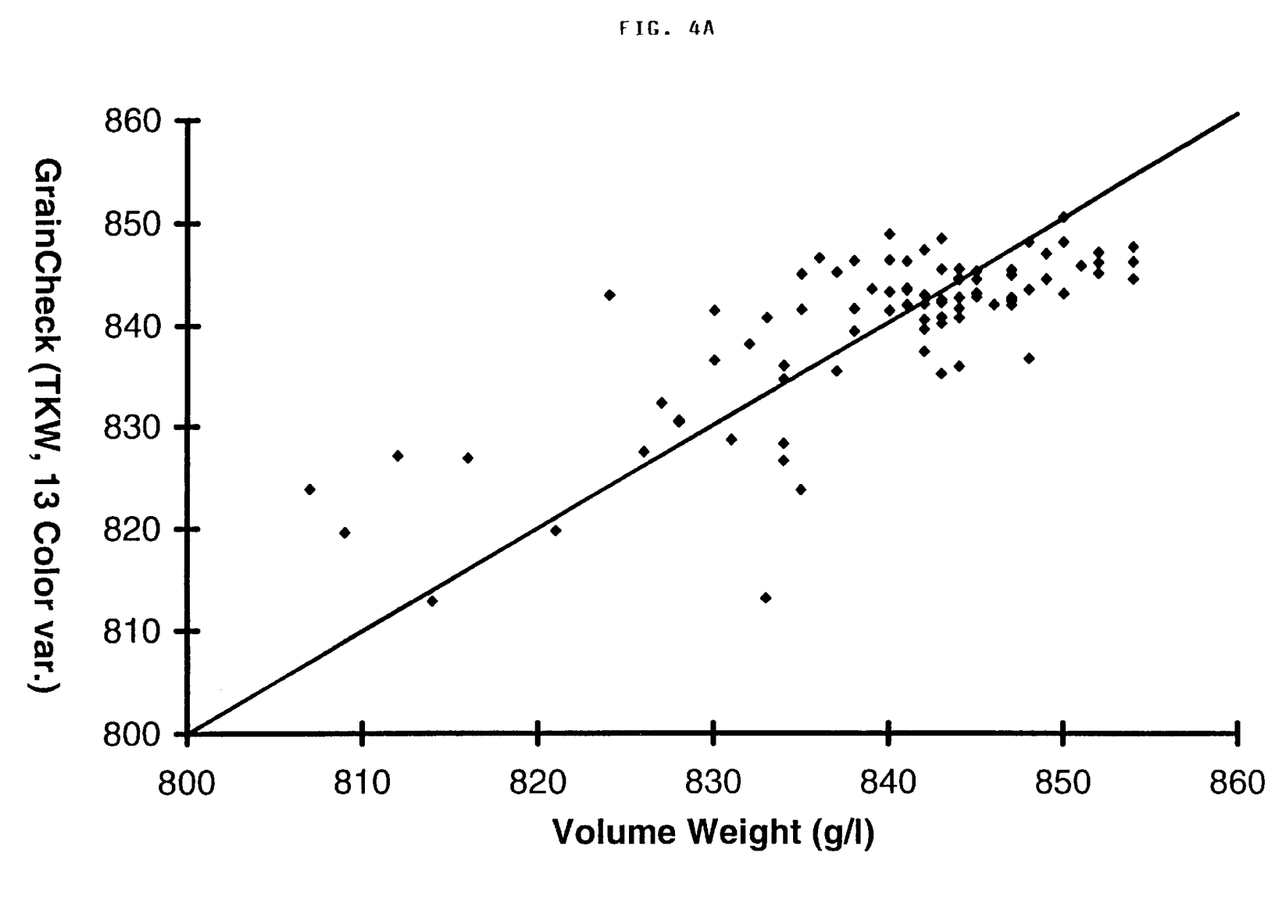
FIGS. 4A, 4B and 4C show the bulk density determined according to the present invention as a function of the actual bulk density by means of a first and a second set of colour input signals and a set of geometric input signals, respectively.

The result of the determination of the bulk density by these input signals is shown in FIG. 4A.

In a second case, use was made of the same input signals as were used in the second case for determining the protein content, i.e. the input signals 8, 15, 16, 26, 27, and the thousand kernel weight.

Figure 4B:
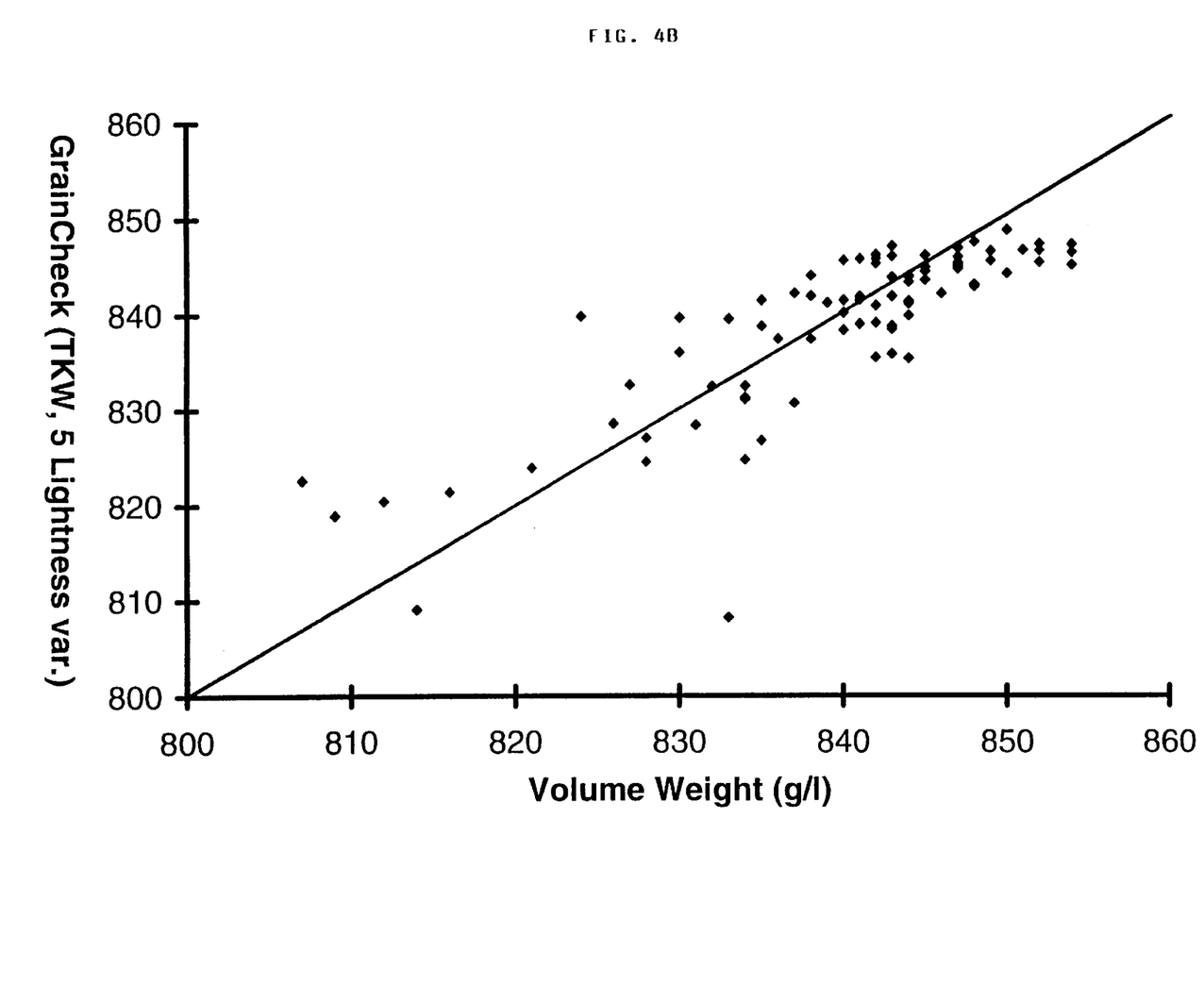

The result of the determination of the bulk density by these input signals is shown in FIG. 4B.

In a third case, use was made of input signals based on geometric parameters, viz. the input signals Nos 1–3 and 17–19, and the mean value of the length values of the sample, the mean value of the width values of the sample, and the mean value of the surface area values of the sample and, as before, the thousand kernel weight.

Figure 4C:
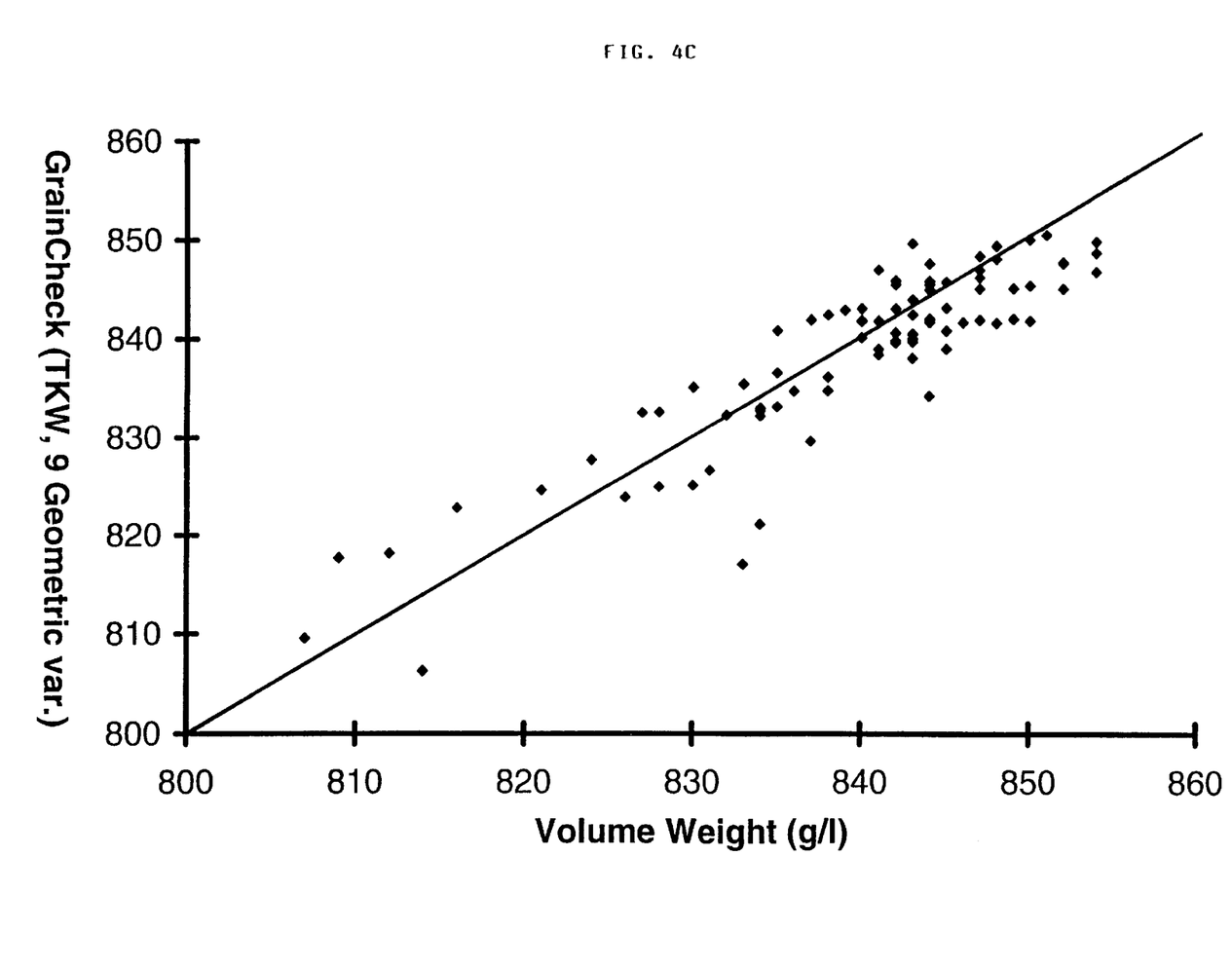

The result of the determination of the bulk density by these input signals is shown in FIG. 4C.

In all determinations of bulk density, the actual bulk density was determined by means of Statmos-Lindell equipment No. 1400 according to the description issued by the National Board of Agriculture. The correlation between measured bulk density and bulk density determined according the invention was 0.76 in the first case, 0.82 in the second case, and 0.89 in the third case.

An embodiment has been described above, in which colour parameters and/or geometric parameters are determined for each kernel and in which the input signals to the neural network are produced by calculation of mean values and dispersion values which mirror the properties of the entire sample. However, it is also possible, at least when determining the protein content, to determine the parameters for each kernel and supply them directly as input signals to the neural network, which in this case can determine the protein content for each individual kernel. It is also possible to determine colour parameters for an entire sample, without registering the colour parameters for the individual kernels. For example, it is possible to determine colour parameters for an image of an entire sample of kernels, in which the kernels are lying close together, without determining the end of one kernel and the beginning of the next.

It has been stated above that flour yield, protein content and bulk density are determined by a neural network. It is, however, feasible in future to explicitly determine the functional connection between the parameters and flour yield, protein content and/or bulk density. In such a case, the neural network can be replaced by a calculation routine which, by means of the thus-determined functions, can calculate flour yield, protein content and/or bulk density.

It has also been described above that the R, G and B values are used as colour parameters. Of course, other colour representations, such as HSI representation, can also be used, which means that, for instance, the term colour parameter should be interpreted in a wide sense and also comprise e.g. hue, intensity and saturation.

Finally, it should be mentioned that the determination of bulk density can also be carried out on other granular products than corn.

We claim:

1. A method of determining the flour yield for a sample of cereal kernels, wherein at least one colour parameter and at least one geometric parameter are determined for the sample, and input signals to a calculation procedure are produced responsive to the colour parameter and the geometric parameter, the flour yield being obtained as an output signal from the calculation procedure.

2. A method as claimed in claim 1, wherein the calculation procedure is carried out by a neural network.

3. A method as claimed in claim 1, wherein said parameter(s) is/are determined for each of the kernels.

4. A method as claimed in claim 1, wherein images of the kernels are produced and said parameter(s) is/are determined on the basis of the images.

5. A method as claimed in claim 4, wherein determination of a colour parameter for a kernel comprises determination of picture element values for at least one picture element component for picture elements which are included in the image of the kernel.

6. A method as claimed in claim 5, wherein determination of a colour parameter comprises determination of the mean value and/or a dispersion measure for said picture element values.

7. A method as claimed in claim 5, wherein determination of a geometric parameter for a kernel comprises the calculation of the number of picture elements included in the image.

8. A method as claimed in claim 1, wherein determination of a geometric parameter for a kernel comprises determination of the width and/or length of the kernel.

9. A method as claimed in claim 1, wherein the weight of a predetermined number of kernels is determined and used in producing input signals to the calculation procedure.

10. A method as claimed in claim 1, wherein the production of input signals to the calculation procedure comprises determination of the mean value for said sample of kernels for at least one parameter.

11. A method of determining the protein content for a sample of cereal kernels, at least one colour parameter being determined for the sample, wherein a dispersion value for said colour parameter over the sample is determined, the dispersion value is used as an input signal to a calculation procedure, the protein content being obtained as an output signal from the calculation procedure.

12. The method of claim 11, wherein said parameter(s) is/are determined for each of the kernels.

13. The method of claim 11, wherein images of the kernels are produced and said parameter(s) is/are determined on the basis of the images.

14. The method of claim 11, wherein the production of input signals to the calculation procedure comprises determination of the mean value for said sample of kernels for at least one parameter.

15. A method of determining the bulk density for a sample of granular products, especially cereal kernels, wherein at least one geometric parameter is determined for the sample, and input signals to a calculation procedure are produced responsive to the geometric parameter, the bulk density being obtained as an output signal from the calculation procedure.

16. A method as claimed in any one of claims 1, 15, 2–10, wherein the production of input signals to the calculation procedure comprises determination of a dispersion value for said sample of kernels for at least one parameter.

17. The method of claim 15, wherein said parameter(s) is/are determined for each of the kernels.

18. The method of claim 15, wherein images of the kernels are produced and said parameter(s) is/are determined on the basis of the images.

19. The method of claim 15, wherein the production of input signals to the calculation procedure comprises determination of the mean value for said sample of kernels for at least one parameter.

20. A method of determining the bulk density for a sample of granular products, especially cereal kernels, at least one colour parameter being determined for the sample, wherein a dispersion value for said colour parameter over the sample is determined, the dispersion value is used as an input signal to a calculation procedure, the bulk density being obtained as an output signal from the calculation procedure.

21. The method of claim 20, wherein said parameter(s) is/are determined for each of the kernels.

22. The method of claim 20, wherein images of the kernels are produced and said parameter(s) is/are determined on the basis of the images.

23. The method of claim 20, wherein the production of input signals to the calculation procedure comprises determination of the mean value for said sample of kernels for at least one parameter.

24. A device for determining the flour yield for a sample of cereal kernels, comprising a device (40) for producing images of the kernels, image analysing means (2) for determining at least one colour parameter and at least one geometric parameter for the sample, means for producing input signals to a calculation means responsive to the colour parameter and the geometric parameter, said calculation means being adapted to determine the flour yield on the basis of the input signals.

25. The device as claimed in claim 24, wherein said calculation means is a neural network.

26. A device for determining the protein content for a sample of cereal kernels, comprising a device (40) for producing images of the kernels, image analysing means (2) for determining at least one colour parameter for the sample, means for producing input signals to a calculation means by calculating a dispersion value for the sample for said colour parameter, the calculation means being adapted to determine the protein content on the basis of the input signals.

27. A device for determining the bulk density for a sample of granular products, especially cereal kernels, comprising a device (40) for producing images of the kernels, image analysing means (2) for determining at least one colour parameter, means for producing input signals to a calculation means by calculating a dispersion value for the sample for said colour parameter, said calculation means being adapted to determine the bulk density on the basis of the input signals.

28. A device for determining the bulk density for a sample of granular products, especially cereal kernels, comprising a device (40) for producing images of the kernels, image analysing means (2) for determining at least one geometric parameter for the sample, means for producing input signals to a calculation means responsive to the geometric parameter, said calculation means being adapted to determine the bulk density on the basis of the input signals.

29. A device as claimed in claim 26, 27 or 28, comprising a feeding device (1) for feeding the kernels past the device (40) for producing images, said feeding device (1) comprising a conveyor belt (18) with recesses (14) and a vibrator (25).

* * * * *